United States Patent [19]

Fischer et al.

[11] Patent Number: 5,300,663

[45] Date of Patent: Apr. 5, 1994

[54] PHOTOCHROMIC NAPHTHACENEQUINONES, PROCESS FOR THEIR PREPARATION AND THE USE THEREOF

[75] Inventors: Walter Fischer, Reinach, Switzerland; Evelyn Fischer, Weil am Rhein, Fed. Rep. of Germany; Ernst Minder, Sissach; Manfred Hofmann, Marly, both of Switzerland; Jürgen Finter, Freiburg, Fed. Rep. of Germany; Heinz Spahni, Frenkendorf, Switzerland

[73] Assignee: Ciba-Geigy Corporation, Ardsley, N.Y.

[21] Appl. No.: 3,066

[22] Filed: Jan. 11, 1993

Related U.S. Application Data

[62] Division of Ser. No. 880,458, May 8, 1992, Pat. No. 5,206,395, which is a division of Ser. No. 639,463, Jan. 10, 1991, Pat. No. 5,177,227.

Foreign Application Priority Data

Jan. 18, 1990 [CH] Switzerland .............. 161/90

[51] Int. Cl.$^5$ .................. C07C 50/24; C07C 5/30
[52] U.S. Cl. ..................... 552/202; 552/200
[58] Field of Search ................. 552/200, 202

[56] References Cited

U.S. PATENT DOCUMENTS 5,001,243  3/1991  Fischer et al. .............. 552/201

FOREIGN PATENT DOCUMENTS 2093475  9/1982  United Kingdom .

OTHER PUBLICATIONS

E. N. Abrahart, Dyes and their Intermediates, p. 8, Pergamon Press (1968).
Y. E. Gerasimenko et al. J. Org. Khim, 7 2413-2415 (1971).
Y. E. Gerasimenko et al. J. Org. Khim 16, 1938-1945 (1980).

Primary Examiner—Marianne M. Cintins
Assistant Examiner—Kimberly J. Kestler
Attorney, Agent, or Firm—George R. Dohmann; Edward McC. Roberts

[57] ABSTRACT

Compounds of formula V, $$\text{(structure with naphthacenequinone core bearing substituents } R_1, R_2, R_3, R_4, \text{ two } =O \text{ and two } OR \text{ groups)} \quad (V)$$

wherein
R is unsubstituted $C_6$-$C_{14}$aryl or $C_6$-$C_{14}$aryl which is substituted by $C_1$-$C_{12}$alkyl, $C_1$-$C_{12}$alkoxy, $C_1$-$C_{12}$alkylthiol, phenyl, benzyl, —CN, —CF$_3$, halogen or —COOR$_5$, and R$_5$ is H, $C_1$-$C_{18}$alkyl, cyclohexyl, cyclopentyl, phenyl, $C_1$-$C_{12}$alkylphenyl, benzyl or $C_1$-$C_{12}$alkylbenzyl, and at least one of the substituents R$_1$ to R$_4$ is an organic thiol, sulfoxyl or sulfonyl group, and the other members R$_1$ to R$_4$ are H, F, Cl or Br, are reversible photochromic systems which can be used for contrast formation or light absorption.

1 Claim, No Drawings

PHOTOCHROMIC NAPHTHACENEQUINONES, PROCESS FOR THEIR PREPARATION AND THE USE THEREOF

This is a divisional of Ser. No. 07/880,458, filed May 8, 1992, now U.S. Pat. No. 5,206,395 which is a divisional of Ser. No. 07/639,463, filed Jan. 10, 1991, now U.S. Pat. No. 5,177,227.

The present invention relates to naphthacene-6,11-and naphthacene-5,12-diones which are substituted in position 5,12 and 6,11 by aryloxy groups and in positions 2, 3, 8 and/or 9 by at least one organic thiol, sulfoxyl or sulfonyl group, to corresponding 5,12- and 6,11-dichloronaphthacenediones containing thiol groups, to a process for the preparation of said aryloxy-substituted naphthacenediones, and to the use thereof as photochromic systems for contrast formation or light absorption.

In Zhurnal Organicheskoi Khimii, Vol. 7, No. 11, pp. 2413–2415 (1971), Yu. E. Gerasimenko et al. describe 6-phenoxynaphthacene-5,12-dione as a reversible photochromic compound which, when subjected to irradiation with light, forms the orange 5-phenoxynapthacene-6,12-dione (anaquinone). In Zhurmal Organicheskoi Khimii, Vol. 16, No. 9, pp. 1938–1945 (1980), Yu. E. Gerasimenko et al. describe 6,11-diphenoxynaphthacene-5,12-dione, whose photoisomerisation is used for synthesising 6-amino derivatives of 12-phenoxynaphthacene-5,11-dione.

In one of its aspects, the present invention relates to compounds of formula I, or mixtures thereof,

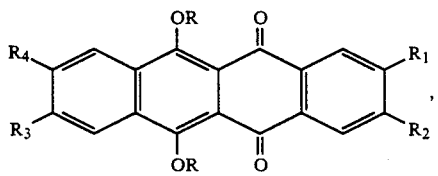

wherein

R is unsubstituted $C_6$–$C_{14}$aryl or $C_6$–$C_{14}$aryl which is substituted by $C_1$–$C_{12}$alkyl, $C_1$–$C_{12}$alkoxy, $C_1$–$C_2$alkylthiol, phenyl, benzyl, —CN, —$CF_3$, halogen or —$COOR_5$, and $R_5$ is H, $C_1$–$C_{18}$alkyl, cyclohexyl, cyclopentyl, phenyl, $C_1$–$C_{12}$alkylphenyl, benzyl or $C_1$–$C_{12}$alkylbenzyl, and at least one of the substituents $R_1$ to $R_4$ is an organic thiol, sulfoxyl or sulfonyl group, and the other members $R_1$ to $R_4$ are H, F, Cl or Br.

R in formula I is preferably unsubstituted or substituted $C_6$–$C_{10}$aryl such as phenyl, or 1-or 2-naphthyl. Preferably R is unsubstituted or substituted phenyl.

The group R may be substituted by one or more, preferably by 1 to 3, substituents. If R is substituted by alkyl, alkoxy or alkylthiol, these radicals may be linear or branched and preferably contain 1 to 6, most preferably 1 to 4, carbon atoms. Exemplary of such radicals are methyl, ethyl, the isomers of propyl, butyl, pentyl, hexyl, heptyl, octyl, nonyl, decyl, and the corresponding alkoxy and alkylthiol radicals. Preferred radicals are methyl, ethyl, n- and isopropyl, n-, iso- and tert-butyl, methoxy, ethoxy, methylthiol and ethylthiol.

If R is substituted by halogen, preferred halogens are bromo, chloro and fluoro.

$R_5$ as alkyl may be linear or branched. Further examples of the alkyl radicals mentioned above are the isomers of tridecyl, tetradecyl, pentadecyl, hexadecyl, heptadecyl and octadecyl. $R_5$ as alkyl preferably contains 1 to 12, most preferably 1 to 6, carbon atoms. $R_5$ as alkylphenyl is preferably $C_1$–$C_6$alkylphenyl, most preferably $C_1$–$C_4$alkylphenyl, for example dodecylphenyl, octylphenyl, hexylphenyl, n-, iso- or tert-butylphenyl, n- or isopropylphenyl, ethylphenyl or methylphenyl. $R_5$ as alkylbenzyl is preferably $C_1$–$C_6$alkylbenzyl, most preferably $C_1$–$C_4$alkylbenzyl, for example dodecylbenzyl, octylbenzyl, hexylbenzyl, n-, iso- or tert-butylphenyl, n- or isopropylbenzyl, ethylbenzyl or methylbenzyl. $R_5$ is preferably H or $C_1$–$C_{18}$alkyl, most preferably $C_1$–$C_{12}$alkyl.

In a preferred embodiment of the invention, R in formula I is unsubstituted or substituted by $C_1$–$C_4$alkyl, $C_1$–$C_4$alkoxy, $C_1$–$C_4$alkylthio, —F, —Cl, —Br or —$COOR_5$, and $R_5$ is H or $C_1$–$C_{18}$alkyl.

Another preferred embodiment of the invention relates to those compounds of formula I, wherein at least one of $R_1$ to $R_4$ is an organic thiol, sulfoxyl or sulfonyl group and the other members $R_1$ to $R_4$ are H.

In yet a further preferred embodiment of the invention, $R_1$ or $R_4$, or $R_1$ and $R_3$ or $R_4$, or $R_1$ and $R_2$, or $R_1$ to $R_4$ are an organic thiol, sulfoxyl or sulfonyl group. The organic thiol, sulfoxyl and sulfonyl group preferably contains 1 to 30, more particularly 1 to 20 and, most preferably, 1 to 12 carbon atoms. $R_1$ to $R_4$ are preferably an organic thiol group. Preferred compounds of formula I are those wherein the organic thiol, sulfoxyl or sulfonyl group has the formula $R_6S$—, $R_6SO$— or $R_6SO_2$—, wherein $R_6$ is $C_1$–$C_{20}$alkyl, $C_3$–$C_8$cycloalkyl, $C_3$–$C_8$cycloalkylmethyl, $C_6$–$C_{10}$aryl or $C_6$–$C_{10}$arylmethyl, and $R_6$ is unsubstituted or substituted by halogen, —CN, —$CF_3$, —$COOR_5$, $C_1$–$C_{12}$alkyl, $C_1$–$C_{12}$alkoxy or $C_1$–$C_{12}$alkylthiol, and $R_5$ has the meanings given above. The organic group is preferably a group of formula $R_6S$—.

$R_6$ may be unsubstituted or may carry one or more, preferably one to three, substituents. If the substituent is halogen, it is preferably fluoro, chloro or bromo. Preferred substituents of $R_5$ are those specified above. If the substituent is alkyl, alkoxy or alkylthiol, said radicals preferably contain 1 to 6, most preferably 1 to 4, carbon atoms. Exemplary of such radicals are those cited above.

In a preferred embodiment of the invention, $R_6$ is unsubstituted or substituted by $C_1$–$C_4$alkyl, $C_1$–$C_4$alkoxy, —F, —Cl or —$COOR_5$, and $R_5$ is H or $C_1$–$C_{18}$alkyl.

$R_6$ as linear or branched alkyl preferably contains 1 to 18 and, preferably, 1 to 12 carbon atoms. Examples of such radicals are cited above. $R_6$ as alkyl is preferably substituted by —$COOR_5$ and then contains in the alkyl moiety preferably 1 to 4, most preferably 1 or 2, carbon atoms. Exemplary of such radicals are $R_5OOC$—$CH_2S$— and $R_5OOC$—$CH_2CH_2S$—.

$R_6$ as cycloalkyl preferably contains 4 to 7, most preferably 5 or 6, ring carbon atoms. Such radicals are typically cyclopropyl, cyclobutyl, cycloheptyl, cyclooctyl and, preferably, cyclopentyl and cyclohexyl.

$R_6$ as cycloalkylmethyl preferably contains 3 to 7, most preferably 5 or 6, ring carbon atoms, and is preferably cyclopentylmethyl and cyclohexylmethyl.

$R_6$ as aryl may be 1- or 2-naphthyl and, preferably, phenyl.

$R_6$ as arylmethyl may be naphthylmethyl and, preferably, benzyl.

In a preferred embodiment of the invention, $R_6$ is unsubstituted or substituted $C_1-C_{12}$alkyl, phenyl or benzyl.

Particularly preferred compounds of formula I are those wherein $R_6$ is $C_1-C_{12}$alkyl or $C_1-C_4$alkyl which is substituted by —$COOR_5$, or is phenyl or benzyl, each unsubstituted or substituted by —F, —Cl, $C_1-C_4$alkyl, $C_1-C_4$alkoxy or —$COOR_5$, and $R_5$, is H or $C_1-C_{18}$alkyl.

In another of its aspects, the present invention relates to a process for the preparation of compounds of formula I, which comprises reacting (a) a compound of formula II

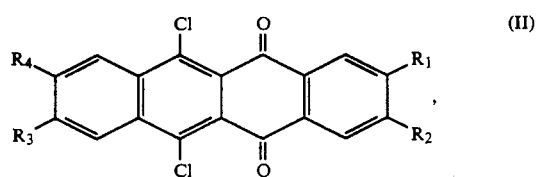

wherein at least one of $R_1$, $R_2$, $R_3$ and $R_4$ is an organic thiol group and the other members $R_1$ to $R_4$ are H, F, Cl or Br, in the presence of a polar aprotic solvent and at elevated temperature, with a compound of formula $RO^{\ominus}M^{\oplus}$, wherein R is as previously defined and M is an alkali metal, and (b) oxidising the resultant compounds, in a manner known per se, to compounds of formula I containing organic sulfoxyl or sulfonyl groups.

The process of the invention is preferably carried out in the temperature range from 50° to 200° C., most preferably from 50° to 150° C. The salts of formula $RO^{\ominus}M^{\oplus}$ may be used as such or produced in situ in the reaction mixture by reacting a suitable phenol with an alkali metal base or an alkali metal carbonate. The salts can be used in equimolar amounts or in excess, for example in an excess of up to 40 mol %.

Typical examples of suitable solvents are N-substituted carboxamides and lactams (such as dimethyl formamide or N-methylpyrrolidone), sulfoxides and sulfones (such as dimethyl sulfoxide, tetramethylene sulfone), or ethers (such as n-dipropyl ether, n-dibutyl ether, tetrahydrofuran or dioxane).

The oxidation of process step (b) can be carried out with alkali metal peroxides, organic peroxides and, preferably, $H_2O_2$. The reaction is normally carried out in a solvent, preferably glacial acetic acid. The reaction temperature may be in the range from room temperature to 150° C., preferably to 100° C.

The compounds of formula I can be isolated and purified by conventional methods, for example by crystallisation and recrystallisation, or by chromatographic methods.

The compounds of formula $RO^{\ominus}M^{\oplus}$ are known or obtainable in known manner by reacting suitable phenols with alkali metal bases or alkali metal carbonates. Particularly suitable alkali metal cations are $Li^{\oplus}$, $Na^{\oplus}$ und $K^{\oplus}$.

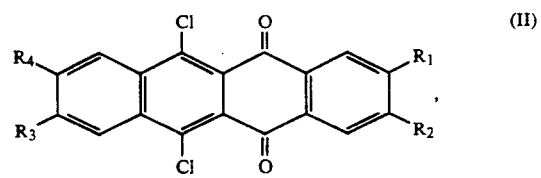

wherein at least one of $R_1$ to $R_4$ is an organic thiol group and the others are H, —F, —Cl or —Br. The preferred meanings of $R_1$ to $R_4$ are the same as those given for the compounds of formula I.

The compounds of formula I are obtainable by the following process:

The reaction of the known compounds of formula III

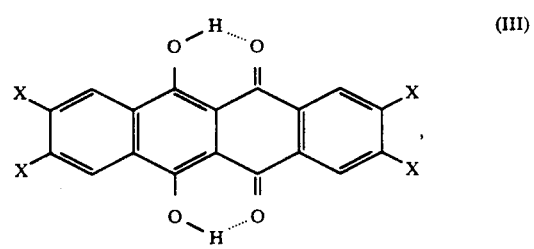

wherein at least one X is halogen, preferably fluoro or chloro, and the other substituents X are halogen or hydrogen, with organothiols of formula $R_1SH$, $R_2SH$, $R_3SH$ and/or $R_4SH$ gives the compound of formula IV which, when unsymmetrically substituted, is obtained as a mixture of tautomers of formulae IV and IVa:

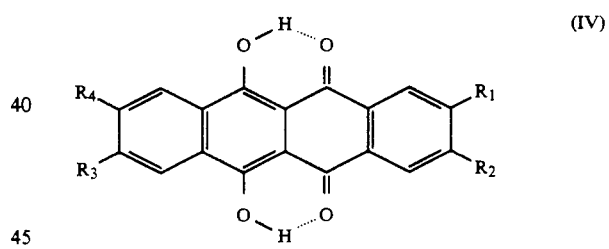

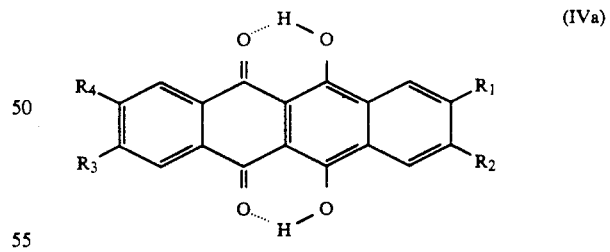

These mixtures of tautomers can be used direct for the preparation of compounds of formula II or separated beforehand, for example by chromatographic methods. The nucleophilic substitution can also be carried out with the corresponding thiolate ions, for example the alkali metal salts, preferably lithium, sodium and potassium salts. The compounds of formula III are obtainable, for example, by reacting appropriately halogenated or non-halogenated phthalic anhydrides with appropriately halogenated or non-halogenated 1,4-dihydroxynaphthalene, in the presence of $B_2O_3$, at elevated temperature.

The compounds of formula IV and IVa can be converted into the compounds of formulae II with customary chlorinating agents such as POCl$_3$.

The compounds of formula I, wherein R$_1$ to R$_4$ are at least one organic thiol group, can also be prepared by chlorinating the compounds of formula III with chlorinating agent first to compounds of formula VI

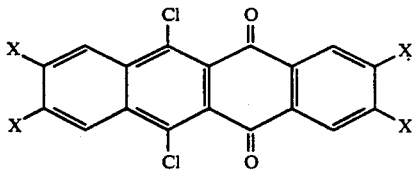

for example with POCl$_3$ in the temperature range from 50° to 200° C. and in the presence of a solvent such as dichlorobenzene, reacting the compounds of formula VI, in the presence of a solvent and an alkali metal carbonate in the temperature range from 50° to 200° C., with not less than 3 mol of R$_1$SH and, if desired, with at least 1 mol of R$_2$SH, R$_3$SH and/or R$_4$SH per mol of compound of formula VI to compounds of formula VII

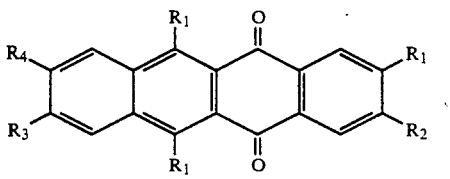

wherein R$_1$ is an organic thiol group and R$_2$ to R$_4$ are an organic thiol group, —H, —F, —Cl or —Br, and then reacting the compounds of formula VII, under oxidative conditions and in the presence of a solvent and an alkali metal carbonate, with a phenol ROH to compounds of formula I. Suitable solvents are those previously mentioned. Preferred alkali metal carbonates are sodium carbonate and, preferably, potassium carbonate. By the expression "oxidative conditions" is meant preferably the presence of air. Surprisingly, in this process only the organic thiol groups R$_1$ are substituted in the positions 5 and 11 regioselectively by phenol groups. The process is conveniently used for the preparation of compounds of formula I, wherein R$_1$ to R$_4$ are organic thiol groups.

The compounds of formula I are crystalline, thermally stable and yellow to orange in colour. They are soluble in organic solvents. They are effective photoinitiators and photosensitisers for photopolymerisable systems which contain ethylenically unsaturated double bonds. Further, the compounds of formula I are reversibly photochromic.

When the compounds of formula I are irradiated, alone or incorporated in a substrate, with light having a wavelength of ca. 300 to 450 nm, a pronounced change in colour towards red is observed. In comparison with 6,11-diphenoxynaphthacene-5,12-dione, the light absorption is displaced to a higher wavelength. The change in colour derives from the photochemical conversion of the paraquinones of this invention into the corresponding anaquinones of formula V. The rate of conversion is surprisingly high and, depending on the amount, thickness of the sample and irradiation intensity, can be less than 3 seconds.

The invention further relates to the anaquinones of formula V

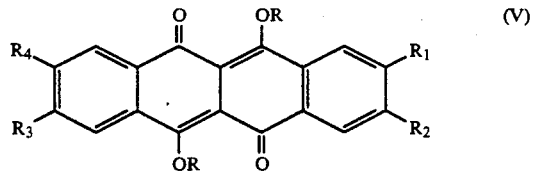

wherein R, R$_1$, R$_2$, R$_3$ and R$_4$ are as previously defined, including the preferred meanings.

The compounds of formula V can be obtained, after irradiating solutions of the compounds of formula I, by removing the solvent, and, as required, purified by conventional methods.

The change in colour is reversible. Renewed irradiation with light having a wavelength of ca. 450 to 550 nm gives the original colour (reformation of the paraquinone structure). It is especially advantageous that this procedure can be repeated several times. The stability of the photochemical conversion of paraquinones to anaquinones and the reverse reaction to paraquinones is surprisingly high and the fatigue even in air or in substrates is correspondingly low. Thus virtually no changes are observed in more than 200 cycles. It is also advantageous that the light absorption necessary for the photochemical conversion lies in the range of the wavelength of commercially available lasers.

The invention further relates to the use of compounds of formula I or V as reversible photochromic structures for contrast formation or light absorption.

The compounds of formula I can be used as photoinitiators and, preferably, as photosensitisers in photopolymerisible systems, in which case they act simultaneously as colour indicators. Thus it is possible to mark irradiated products (for example protective layers, printing plates, offset printing plates, printed circuits, solder masks) and to distinguish them from non-irradiated products and, in product control, to sort out imperfectly irradiated products before or after development.

The major advantage in using the compounds of formula I as colour indicators lies in the increase of the sensitiser action. Components normally used as colour change systems generally effect a diminution of the photosensitivity.

The compounds of formula I or V can also be used by themselves, in solution or incorporated in polymers as photochemically modifiable colour indicators or as photochemically modifiable circuit components.

The compounds of formula I can also be used in organic or inorganic glass as photochemically modifiable colour filters, for example in glass for sunglasses, contact lenses, windows and mirrors.

The invention further relates to a radiation-sensitive composition comprising
a) a radiation-sensitive organic material, and
b) at least one compound of formula I or V or a mixture thereof.

The compounds of formulae I and V or mixtures thereof may be present in an amount of 0.001 to 20% by weight, preferably 0.001 to 10% by weight and, most preferably, 0.01 to 5% by weight, based on component a).

Radiation-sensitive and hence also photostructurable materials are known. They may be positive or negative systems. Such materials are described, for example, by E. Green et al. in J. Macromol. Sci.; Revs. Macromol. and Chem., C21(2), 187-273 (1981 to 1982) and by G. A. Delzenne in Adv. Photochem., 11, S. 1-103 (1979).

The radiation-sensitive organic material is preferably a1) a non-volatile monomeric, oligomeric or polymeric substrate containing photopolymerisable or photodimerisable ethylenically unsaturated groups, a2) a cationically curable system, or a3) photocrosslinkable polyimides.

Photopolymerisable substances are typically acrylates and, preferably, methacrylates of polyols, for example ethylene glycol, propanediol, butanediol, hexanediol, bis(hydroxymethyl)cyclohexane, polyoxyalkylenediols such as di-, tri- or tetraethylene glycol, di- or tri-1,2-propylene glycol, trimethylolmethane, trimethylolethane or trimethylolpropane and pentaerythritol, which may be used by themselves, in mixtures and in admixture with binders.

Exemplary of photodimerisable substances are homo- and copolymers which contain cinnamic acid groups or substituted maleimidyl compounds in side groups or chalcone groups in the polymer chain.

Preferred compositions are those wherein component a1) is a homo- or copolymer of acrylates, methacrylates or maleates whose ester groups contain a radical of formula

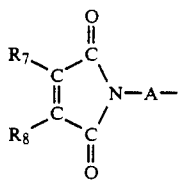

wherein A is linear or branched unsubstituted or hydroxyl-substituted $C_2$-$C_{12}$alkylene, cyclohexylene or phenylene, and $R_7$ and $R_8$ are each independently of the other chloro or bromo, phenyl or $C_1$-$C_4$alkyl, or $R_7$ and $R_8$, when taken together, are trimethylene, tetramethylene or

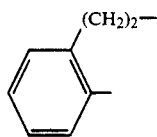

Such polymers are disclosed, for example, in U.S. Pat. No. 4,193,927.

The photopolymerisable or photodimerisable substances can contain further additives customarily used for processing or application, as well as other photoinitiators or photosensitisers.

The cationically curable systems are preferably epoxy compounds containing at least two epoxy groups in the molecule and in which a photoinitiator is incorporated. Suitable photoinitiators are typically cyclopentadienylarene metal salts, cyclopentadienyl metal carbonyl salts and onium salts which are described in the above mentioned publications. The curable systems may contain additives customarily used for processing and application.

Photosensitive polyimides are disclosed, for example, in DE-A-1 962 588, EP-A-0 132 221, EP-A-0 134 752, EP-A-0 162 017, EP-A-0 181 37 and EP-A-0 182 745.

The composition of this invention is applied by known methods as layer to substrates and either a protective layer is produced by irradiation over the surface, or a relief image is produced by irradiation through a photomask or by locally defined irradiation with a guided laser beam or by holographic methods and subsequent development.

In another of its aspects, the invention relates to a composition comprising a) a colourless organic solvent, a polymer or an organic glass or a compound glass, and b) dissolved, incorporated therein or present as layer on at least one surface, a compound of formula I or V or a mixture thereof. Component b) is preferably present in an amount of 0.001 to 20% by weight, preferably 0.001 to 10% by weight and most preferably, 0.01 to 5% by weight, based on component a). Organic solutions can be used for coating other substances, for example solid substrates such as inorganic glasses which can then be used as photochemically modifiable substrates. The compounds of formula I can also be sublimed on to substrates. The coated substrates can be provided with a protective layer of, for example, transparent polymers. Solid substrates can also be coated with compositions which contain a polymer and at least one compound of formula I or V. Suitable solvents are typically hydrocarbons, halogenated hydrocarbons, ketones, carboxylic acid esters and lactones, N-alkylated acid amides and lactams, alkanols and ethers.

Exemplary of suitable polymers are thermoset plastics, thermoplastics and structurally crosslinked polymers. The polymers are preferably transparent. Such polymers and organic glasses are known to those skilled in the art. The incorporation of the compounds of the invention is effected by known methods, for example by dissolving methods and removing the solvent, calendering or extrusion. The compounds of this invention can also be incorporated in the substrates before, during or after their synthesis.

The invention also relates to a process for the preparation of coloured materials under the influence of light, which comprises incorporating a compound of formula I or V in the material and then irradiating said material with light.

The invention further relates to the use of compounds of formula I as photosensitisers and colour indicators or photochemically modifiable colour filters under the influence of light.

In another of its aspects, the invention relates to the use of a compound of formula I or V for the reversible optical storage of information, which information is written with light, preferably laser light, into a memory-active layer containing said compound. The written information can be erased, preferably with laser light, thus affording the possibility of cyclic writing-in and erasing.

To produce a memory-active layer, the compound of formula I or V can be dissolved in a transparent matrix by methods described above and applied in a thin layer to a flat substrate. The thickness of the memory-active layer is ca. 0.1-100 μm, preferably 0.3-3 μm.

The information can be written by scanned, holographic or photographic irradiation of the memory-active layer with spectral, preferably coherent, laser light in the wavelength range of 440-550 nm, preferably 480-530 nm.

Reading out can be effected with reduced irradiation intensity at the wavelength in which the information is written via the locally altered transmission, reflectance, refraction or fluorescence of the memory-active layer.

Erasure can be made by pin-point or spread irradiation of the memory-active layer containing the compounds of formula I and/or V in the wavelength range of 300–450 nm, preferably 300–400 nm.

One advantage of the utility of this invention is that the wavelengths necessary for writing in, reading out and erasing are in the range of commercially available lasers (for example argon ion lasers: 488/514 nm and 351/363 nm; neodym-YAG lasers: 532 nm and 355 nm; XeF excimer lasers: 351 nm; HeCd lasers: 325 and 442 nm, with frequency doubling and trebling).

A further advantage is the high contrast of absorption obtainable between the written and erased state in the range of 450–550 nm and the wide dynamic range associated therewith of the memory-active layer.

Another advantage is that the quantum yield when writing is fairly low, so that the danger of overwriting when reading out is greatly diminished.

Conversely, it is also advantageous that the quantum yield when erasing is fairly high, thus making possible a rapid erasure over a large area.

Yet a further advantage is that, when reading out, the compound fluoresces and hence makes possible a highly sensitive detection of the memory status via the fluorescence. The fact that the energy pulsed in for reading out dissipates substantially via the fluorescence and not thermally also counteracts an undesirable heating of the memory-active layer.

Another advantage is the high photochemical stability of the compound and the great number of writing/erasing cycles thereby obtainable.

Finally, yet another advantage is the possibility of cyclic data refreshing by admixture of a suitable quantum of light of the erasure wavelength during reading out.

The invention is illustrated by the following Examples.

A) Preparation of the starting compounds

EXAMPLE A1

2,3,8,9-Tetraphenylthio-6,11-dihydroxynaphthacene-5,12-dione 50 g (116.8 mmol) of 2,3,8,9-tetrachloro-6,11-dihydroxynaphthacene-5,12-dione, 77.22 g (700.8 mmol) of thiophenol, 129.15 g (934 mmol) of potassium carbonate and 400 ml of dimethyl sulfoxide (DMSO) are stirred for 1 day at 100° C. The mixture is poured into a dilute aqueous solution of HCl and stirred. The red crude product is isolated by filtration, washed with water, dried at 140° C. under vacuum, then extracted three times by boiling with cyclohexanone and dried once more. Yield: 80.11 g (95%); melting point >260° C. MS: 722 (M+; base peak).

EXAMPLE A2

2,3,8,9-Tetraethylthio-6,11-dihydroxynaphthacene-5,12-dione

The title compound is prepared as described in Example A1 using ethyl mercaptan. Yield: 89%; m.p.: 240° C. (decomposition); MS: 530 (M+; base peak).

EXAMPLE A3

2,3,8,9-Tetra-n-dodecyl-6,11-dihydroxynaphthacene-5,12-dione

The title compound is prepared as described in Example A1, using dodecyl mercaptan at 120° C. with the addition of dimethyl formamide (DMF): Yield: 87%; m.p.: 66°–76° C.; MS: 1090 (M+; base peak).

EXAMPLE A4

2,3,8,9-Tetra(p-methylphenylthio)-6,11-dihydroxynaphthacene-5,12-dione.

The title compound is prepared as described in Example A1 using p-thiocresol at 100° C. Yield: 83%; m.p.: >265° C.; MS: 778 (M+; base peak).

EXAMPLE 5A 2,3,8,9-Tetra(p-chlorophenylthio)-6,11-dihydroxynaphthacene-5,12-dione.

The title compound is prepared as described in Example A1 using p-chlorothiophenol at 120° C. Yield: 82%; m.p.: >300° C.; MS: 858/860/862/864 (M+; base peak).

EXAMPLE A6

2,3,8,9-Tetra(3-methoxyphenylthio)-6,11-dihydroxynaphthacene-5,12-dione.

The title compound is prepared as described in Example A1 using m-methoxythiophenol at 100° C. Yield: 90%; m.p.: 287°–92° C.; MS: 842 (M+; base peak).

EXAMPLE 7A

2-Phenylthio-6,11-dihydroxynaphthacene-5,12-dione (mixture of tautomers)

4.62 g (15 mmol) of 2-fluoro-6,11-dihydroxynaphthacene-5,12-dione (mixture of tautomers), 2.2 g (20 mmol) of thiophenol, 11.06 g (80 mmol) of potassium carbonate and 50 ml of dimethyl sulfoxide (DMSO) are stirred for 22 hours at 70° C. The mixture is poured into 600 ml of a 0.5M solution of HCl in H$_2$O. After stirring for 15 minutes, the precipitate is isolated by filtration, washed 3 times with water and once with methanol, dried at 120° C. under vacuum and recrystallised from toluene. Yield: 3.02 g (51%), m.p. >260° C.; MS: 398 (M+; base peak), 388, 295, 261, 233, 199, 176.

The procedure of this Example is repeated, using 2-chloro-6,11-dihydroxynaphthacene-5,12 dione (mixture of tautomers) and appropriately substituted thiophenols at 80° C., to give the compounds A7a to A7e (mixtures of tautomers).

A7a: 2- and 9-(4′-Chlorophenylthio)-6,11-dihydroxynaphthacene-5,12-dione. Yield: 95%, m.p.: 225°–227° C.; mass spectrum: 432 (M+; base peak).

A7b: 2- and 9-(4′-Fluorophenylthio)-6,11-dihydroxynaphthacene-5,12-dione. Yield: 89%, m.p.: 192°–200° C.; mass spectrum: 416 (M+; base peak).

A7c: 2- and 9-(4′-Methoxyphenylthio)-6,11-dihydroxynaphthacene-5,12-dione. Yield: 84%, m.p.: 170°–175° C.; mass spectrum: 428 (M+: base peak)

A7d: 2- and 9-(4′-Ethoxycarbonylphenylthio)-6,11-dihydroxynaphthacene-5,12-dione. Yield: 95%, m.p.: 140°–150° C.; mass spectrum: 470 (M+: base peak).

A7e: 2- and 9-(3′-Methoxyphenylthio)-6,11-dihydroxynaphthacene-5,12-dione. Yield: 90%, m.p.: 145°–155° C.; mass spectrum: 428 (M+: base peak).

EXAMPLE 8

2-n-Dodecylthio-5,11-dihydroxynaphthacene-5,12-dione (mixture of tautomers)

1.54 g (5 mmol) of 2-fluoro-5,11-dihydroxynaphthacene-5,12-dione (mixture of tautomers), 5.53 g (40 mmol) of $K_2CO_3$, 2.02 g (10 mmol) of n-dodecanethiol and 15 ml of DMSO are stirred for 18 hours at 90° C. The mixture is poured into a dilute aqueous solution of HCl. The mixture is stirred for 10 minutes and the product is then isolated by filtration, washed 3 times with water and once with methanol, dried at 80° C. under vacuum and recrystallised from toluene. Yield: 2.40 g (98%), m.p. 146°-148° C.; MS: 398 (M+: base peak), 388, 295, 261, 233, 199, 176.

EXAMPLE A9

2,3,6,8,9,11-Hexachloronaphthacene-5,12-dione 30 g (70 mmol) of 2,3,8,9-tetrachloro-6,11-dihydroxynaphthacene-5,12-dione, 60 ml of $POCl_3$ and 500 ml of o-dichlorobenzene are stirred for 90 hours under reflux. Then excess $POCl_3$ together with the o-chlorobenzene is removed by distillation until the volume of the reaction mixture is still ca. 300 ml. After cooling, the precipitate is isolated by filtration, washed repeatedly with water and aqueous sodium carbonate solution, dried and stirred in cyclohexane. The product is isolated by filtration and then dried. Yield: 28.6 g (88%), m.p.: >260° C.

B) Preparation of inventive compounds

EXAMPLE B1

2,3,8,9-Tetraethylthio-6,11-bis(3,5-dichlorophen-1-oxy)naphthacene-5,12-dione a) 0.30 g (0.57 mmol) of the compound of Example A2 are stirred under reflux in 20 ml of phosphoroxy chloride for 8 days. With cooling, the reaction mixture is poured into water and is stirred. The precipitate is isolated by filtration, washed with water and dried. Chromatography with copious methylene chloride over silica gel gives 0.13 g (40%) of 2,3,8,9-tetraethylthio-6,11-dichloro-naphthacene-5,12-dione, m.p. >260° C.; MS: 566/568/570 (base peaks, M+).

b) 0.07 g (0.12 mmol) of this compound, 0.05 g (0.31 mmol) of 3,5-dichlorophenol, 0.07 g (0.49 mmol) of potassium carbonate and 3 ml of DMSO are stirred for 18 hours at 70° C. The mixture is poured into water/toluene and the organic phase is dried over sodium sulfate and concentrated by evaporation. The crude product (0.08 g; 80%) is yellowish orange. The following $\lambda_{max}$ values are obtained (UV/VIS spectrum, solution in toluene): 439, 466 und 495 nm. The crude product contains a minor amount of 2,3,8,9-tetraethylthio-6,12-bis(3,5-dichlorophen-1-oxy)naphthacene-5,11-dione.

EXAMPLE B2

2,3,8,9-Tetraethylthio-6,11-diphenoxynaphthacene-5,12-dione a) Process a) of Example B1 is repeated, starting from the compound of Example A1 with the addition of dichlorobenzene as solvent, at 160° C., to give 2,3,8,9-tetraphenylthio-6,11-dichloronaphthacene-5,12-dione: MS: 758/760/762 (base peaks, M+).

b) Process b) of Example B1 is repeated, reacting this compound with phenol to give the yellowish orange title compound. UV/VIS spectrum in toluene: $\lambda_{max}$=432 nm.

EXAMPLE B3

2-Phenylthio-6,11-diphenoxynaphthacene-5,12-dione (A) and 9-phenylthio-6,11-diphenoxynaphthacene-5,12-dione (B)

a) 2.90 (7.28 mmol) of the compound of Example A7 are stirred under reflux in 29 ml of $POCl_3$ for 2 days. With efficient stirring, the mixture is charged into 300 ml of ice-water and stirred. The suspension is extracted with toluene and the organic phases are filtered, washed with 2N NaOH solution, dried over sodium sulfate and concentrated by evaporation. Yield: 2.73 g (86%). Fractional crystallisation from toluene gives both isomers in pure form:

2-phenylthio-6,11-dichloronaphthacene-5,12-dione: 0.38 g; m.p. 201°-3° C.; MS: 434/436/438 (M+);

9-phenylthio-6,11-dichloronaphthacene-5,12-dione: 0.13 g; m.p. 181°-4° C.; MS: 434/436/438 (M+).

b) 2 g (4.59 mmol) of the crude product (mixture of isomers), 1.08 g (11.49 mmol) of phenol, 2.54 g (18.38 mmol) potassium carbonate and 15 ml of DMSO are stirred for 40 minutes at 60° C. The mixture is cooled, taken up in THF/toluene and a dilute solution of HCl and extracted. The organic phases are washed twice with water, dried over sodium sulfate and concentrated by evaporation. Flash chromatography with methylene chloride over silica gel gives both isomers in pure form.

More rapidly eluting product:

Title compound A: 1.12 g of crude product recrystalliosed from toluene: 0.78 g (31%), m.p. 160°-3° C.; MS: 550 (M+/base peak).

More slowly eluting product

Title compound B: 0.77 g of crude product, recrystallised from toluene: 0.72 g (29%), m.p. 150°-3° C.; MS (m/e): 550 (M+) (base peak).

EXAMPLES B4-B8

Process b) of Example B3 is repeated by reacting the mixture of isomers of Example B3a) with the appropriate phenol to give the isomeric mixtures of the following compounds:

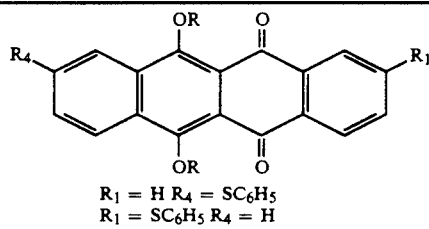

$R_1$ = H  $R_4$ = $SC_6H_5$
$R_1$ = $SC_6H_5$  $R_4$ = H

| R | Mass spectrum [M+] | Yield [Y] | Melting point [°C.] |
|---|---|---|---|
| —⟨⟩—CO₂CH-n-C₆H₁₃ with CH₃ | 862 | 94 | Oel |
| —⟨⟩ with Br | 706 | 80 | 205-230° C. |

-continued

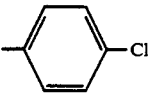

R₁ = H  R₄ = SC₆H₅
R₁ = SC₆H₅  R₄ = H

| R | Mass spectrum [M+] | Yield [Y] | Melting point [°C.] |
|---|---|---|---|
| 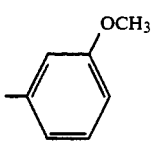—Cl | 618 | 77 | 228–245° C. |
| 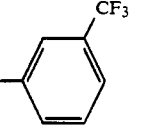—OCH₃ | 610 | 80 | 177–182° C. |
| —⌬—CF₃ | 686 | 74 | 215–234° C. |

EXAMPLE B9

2-n-Dodecylthio-6,11-diphenoxynaphthacene-5,12-dione (A) and
9-n-dodecylthio-6,11-diphenoxynaphthacene-5,12-dione (B)

a) Process a) of Example B3 is repeated, using n-dodecyl mercaptan and the mixture of tautomers of Example A8. Chromatographic separation of the crude product (yield 86%) over silica gel with toluene gives:

2-n-dodecylthio-6,11-dichloronaphthacene-5,12-dione: 0.29 g; m.p. 120°–125° C.;
9-n-dodecylthio-6,11-dichloronaphthacene-5,12-dione: 0.29 g; m.p. 113°–114° C.;

b) 0.20 g (0.38 mmol) of 2-n-dodecylthio-6,11-dichloronaphthacene-5,12-dione, 0.09 g (0.95 mmol) of phenol, 0.21 g (1.52 mmol) of potassium carbonate and 2 ml of DMSO are stirred for 75 minutes at 60° C. The mixture is taken up in toluene and extracted twice with toluene. The toluene phases are washed twice with water, dried over sodium sulfate and concentrated by evaporation. Recrystallisation from ether/pentane gives 0.13 g (54%) of the title compound A, m.p. 165°–8° C.; MS: 642 (M+; base peak).

The title compound B is obtained in analogous manner from
9-n-dodecylthio-6,11-dichloronaphthacene-5,12-dione: Yield after recrystallisation from ether/pentane: 0.13 g (54%), m.p. 143°–5° C.; MS: 642 (M+; base peak).

EXAMPLES B10–B14

Naphthacenediones containing substituted phenylthio groups

The compounds A7a to A7e are chlorinated as in process B3a and reacted in accordance with process B3b with phenol to give the corresponding mixtures of isomers:

EXAMPLE B10

2- and 9-(4'-Chlorophenylthio)-6,11-diphenoxynaphthacene-5,12-dione a) 2- and 9-(4'-Chlorophenylthio)-6,11-diphenoxynaphthacene-5,12-dione: reaction time: 7 days, yield: 64%, mass spectrum: 468 (M+: base peak).

b) Title compound: yield: 70%, m.p.: >250° C., mass spectrum: 584 (M+: base peak).

EXAMPLE B11

2- and 9-(4'-Fluorophenylthio)naphthacene-6,11-diphenoxynaphthacene-5,12-dione a) 2- and 9-(4'-Fluorophenylthio)-6,11-dichloronaphthacene-5,12-dione: reaction time: 8 days, yield: 68%, mass spectrum: 452 (M+: base peak).

b) Title compound: yield: 61%, m.p.: >250° C., mass spectrum: 568 (M+: base peak).

EXAMPLE B12

2- and 9-(4'-Methoxyphenylthio)-6,11-phenoxynaphthacene-5,12-dione a) 2- and 9-(4'-Methoxyphenylthio)-6,11-dichloronaphthacene-5,12-dione: reaction time: 4 days, yield: 85%, mass spectrum: 464 (M+: base peak).

b) Title compound: yield: 66%, m.p.: 200°–206° C., mass spectrum: 580 (M+: base peak).

EXAMPLE B13

2- and 9-(4'-Ethoxycarbonylphenylthio)-6,11-diphenoxynaphthacene-5,12-dione.

a) 2- and 9-(4'-Ethoxycarbonylphenylthio)-5,11-dichloronaphthacene-5,12-dione: reaction time: 7 days, yield: 25%, mass spectrum: 506 (M+: base peak).

b) Title compound: yield: 83%, m.p.: 190°–210° C., mass spectrum: 622 (M+: base peak).

EXAMPLE B14

2- and 9-(3'-Methoxyphenylthio)-6,11-diphenoxynaphthacene-5,12-dione a) 2- and 9-(3'-Methoxyphenylthio)-6,11-dichloronaphthacene-5,12-dione: reaction time: 6 days, yield: 85%, mass spectrum: 464 (M+: base peak).

b) Title compound: yield: 75%, m.p.: 160°–170° C., mass spectrum: 580 (M+: base peak).

EXAMPLE B15 of 2,3- and 8,9-Di(phenylthio)-6,11-diphenoxynaphthacene-5,12-dione (mixture of isomers)

a) 2,3- and 8,9-Diphenylthio-6,11-dihydroxynaphthacene-5,12-dione 5 g (13.9 mmol) of 2,3- and 8,9-dichloro-6,11-dihydroxynaphthacene-5,12-dione, 3.37 g (30.6 mmol) of thiophenol, 6,81 g (49.3 mmol) of K₂CO₃ and 50 ml of dimethyl sulfoxide are stirred for 3 hours at 65° C. The mixture is charged to dilute hydrochloric acid and the red crystals are isolated by filtration, washed with water and dried at 120° C. under vacuum. Recrystallisation from toluene gives 4.5 g of product, m.p. >270° C.

b) 2,3- and 8,9-Diphenylthio-6,11-dichloronaphthacene-5,12-dione 2.5 g of the mixture of iosmers obtained in step a) and 45 ml of POCl$_3$ are stirred under reflux for 4 days. The mixture is poured into water and the crystals are isolated by filtration, washed repeatedly with water and then dissolved in toluene. The separated organic phase is washed with dilute aqueous sodium hydroxide and then with water, subsequently dried over sodium sulfate and concentrated by evaporation. After stirring the residue in toluene with the addition of alumina, followed by filtration and concentration, 1.8 g of yellow crystals of m.p. 240°–243° C. are obtained.

c) 1.7 g (3.13 mmol) of the mixture of isomers obtained in step b), 0.74 g (7.82 mmol) of phenol, 1.3 g (9.4 mmol) of potassium carbonate and 30 ml of dimethyl sulfoxide are stirred for 1 hour at 85° C. The reaction mixture is then poured into dilute hydrochloric acid and the crystalline precipitate is isolated by filtration and taken up in a 1:1 mixture of tetrahydrofuran/toluene. The organic phase is washed with water, dried over sodium sulfate and then concentrated by evaporation. Recrystallisation from toluene gives 1.14 g (55%) of the title compound in the form of yellow crystals of m.p.>270° C., mass spectrum: 658 ((M+, base peak). A reversible change from yellowish orange to red is observed by irradiating a solution of the compound in toluene.

EXAMPLE B16

2,8- and 2,9-Diphenylthio-6,11-diphenyloxynaphthacene-5,12-dione a) 2,6,8,11- and 2,6,9,11-Tetrachloro-naphthacene-5,12-dione 20 g (55.8 mmol) of 2,8- and 2,9-dichloro-6,11-dihydroxynaphthacene-5,12-dione (mixture of tautomers), 100 ml of POCl$_3$ and 400 ml of o-dichlorobenzene are heated at reflux for 5 days. The reaction mixture is then concentrated to half its volume and extracted with methylene chloride. The organic phase is separated, washed with water and a saturated solution of sodium chloride, dried over sodium sulfate and then concentrated by evaporation. The residue is chromatographed twice over silica gel and recrystallised from xylene to give 11.2 g (51%) of product.

b) 2,6,8,11- and 2,6,9,11-Tetraphenylthionaphthacene-5,12-dione 2 g (5.05 mmol) of the mixture of isomers obtained in step a), 5.58 g (40.4 mmol) of potassium carbonate, 3.34 g (30.3 mmol) of thiophenol and 14 ml of dimethyl sulfoxide are stirred for 1 day at 60° C. and for 4 hours at 120° C. The reaction mixture is then poured into dilute hydrochloric acid and extracted with toluene. The organic phase is washed with water, dried over sodium sulfate and concentrated by evaporation. The crude product is chromatographed over silica gel to give 1.38 g (40%) of the title compound in the form of a red oil.

c) 0.3 g (0.434 mmol) of the compound obtained in step b), 0.14 g (1.52 mmol) of phenol, 0.24 g (1.74 mmol) of potassium carbonate and 10 ml of dimethyl sulfoxide are stirred at 100° C. for 6 hours while introducing air. After cooling, the reaction mixture is taken up in toluene and the organic phase is washed in succession with dilute hydrochloric acid, 1N aqueous sodium hydroxide and then with water, dried over sodium sulfate and concentrated by evaporation. The crude product is chromatographed, with the exclusion of light, with toluene over silica gel to give 0.12 g (43%) of the title compound in the form of an orange oil. Mass spectrum: 658 (M+: base peak). A reversible colour change from yellowish orange to red is observed by irradiating a solution of the compound in toluene.

EXAMPLE B17

2,3,8,9,-Tetraphenylthio-6,11-diphenoxynaphthacene-5,12-dione a) 2,3,6,8,9,11-Hexaphenylthionaphthacene-5,12-dione 10 g (21.5 mmol) of compound A9, 23.7 g (215 mmol) of thiophenol, 32.69 g (237 mmol) of potassium carbonate and 200 ml of dimethyl sulfoxide are stirred for 18 hours at 80° C. After cooling, the reaction mixture is poured into 2N hydrochloric acid and the precipitate is isolated by filtration and washed with water. The crystalline precipitate is extracted repeatedly with hot cyclohexane and then dried, giving 16.8 g (86%) of product in the form of red crystals. Melting point:>260° C., mass spectrum: 690 (M+: base peak).

b) 8 g (8.82 mmol) of the compound prepared in step a), 4.14 g (44.1 mmol) of phenol, 7.31 g (52.9 mmol) of potassium carbonate and 150 ml of dimethyl sulfoxide are stirred for 9 hours at 100° C. with the exclusion of air and then cooled. The reaction mixture is then poured into 2N hydrochloric acid and the precipitate is isolated by filtration, washed repeatedly with water and dried. Recrystallisation from toluene gives 5.33 g (69%) of the title compound, m.p.>270° C.; mass spectrum: 874 (M+); 782 and 690 (each —C$_6$H$_5$). A reversible colour change from yellow to red is observed by irradiating a solution of the compound in toluene.

EXAMPLE 18

2-Phenylsulfonyl-6,11-diphenoxynaphthacene-5,12-dione 4 g (7.26 mmol) of compound B3 (mixture of isomers), 5 ml of 30% aqueous H$_2$O$_2$ and 70 ml of glacial acetic acid are stirred for 8 hours at 80° C. The mixture is taken up in a mixture of water/tetrahydrofuran/toluene and the organic phase is separated, washed with an aqueous solution of sodium bisulfite and twice with water, dried over sodium sulfate and concentrated by evaporation. Recrystallisation from toluene gives 2.08 g (49%) of the title compound, m.p.>260°–270° C.; mass spectrum: 582 (M+: base peak). A reversible colour change from yellow to orange is observed by irradiating a solution of the compound in toluene.

C) Use Examples

EXAMPLE C1

Solutions of compounds of Examples B1 to B3 and B9 are irradiated with a xenon lamp (120 W) to form the corresponding anaquinones; for example

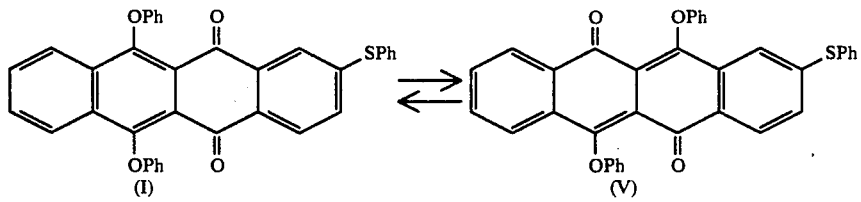

The anaquinones can be isolated by evaporating the solvent. Further particulars are given in the following table.

| Compound of Example | Solvent | Colour change | UV/VIS spectrum $\lambda_{max}$(nm) I | V |
|---|---|---|---|---|
| B 1 | toluene | yellowish orange to red | 439, 469, 495 | 498, 552 |
| B 2 | toluene | yellowish orange to red | 432 | 493, 528 |
| compound A of B 3 | acetonitrile | yellow to red | 408 | 467, 503 |
| compound B of B 3 | acetonitrile | yellow to red | 393 | 467, 503 |
| compound A of B 9 | acetonitrile | yellow to red | 411 | 469, 502 |
| compound B of B 9 | acetonitrile | yellow to red | 395 | 469, 502 |

EXAMPLE C2

Films prepared with inventive compounds 100 mg of polystyrene and 3.05 mg of compound A (film I) and compound B of Example B3 (film II) are each dissolved in 8.3 g of toluene. One fifth of each solution is poured on to heated glass plates each of 60°, 70°, 80°, 90° and 100° C. and the toluene is evaporated. The films are yellow and transparent. Film I is irradiated with UV light (334 nm, laser beam, expanded to 4.5 mm) until saturated (red coloration) and placed in the path of rays of a diode array spectrometer. Transmission spectra are recorded periodically during irradiation with visible light (488 nm, 125 mW/cm$^2$). The photochemical reaction is monitored on the basis of the change of the spectrum at 470 nm. The conversion rate during this irradiation gives a time constant of the conversion of 2.6 s. A laser intensity of 25 mW/cm$^2$ at 325 nm suffices for the reverse reaction for an identical speed.

Film I is irradiated at 325 nm with an intensity of 125 mJ/cm$^2$, afterwards at 488 nm with an intensity of 625 mJ/cm$^2$. A spectrum is recorded after every 10 cycles and compared with the spectrum before the first cycle. No permanent change in the sample can be measured after 150 alternating exposures. The energy density necessary for the photochemical reaction also remains the same.

EXAMPLE C3

Irradiation cycles using a polystyrene film 100 mg of polystyrene and 3 mg of compound B3 are dissolved in 8.3 g of toluene and poured on to heated glass plate of 70° C. The solvent is evaporated off to give a yellow transparent film having a thickness of 10 μm. The film is mounted on a quartz glass plate in the testing chamber of a spectrophotometer and irradiated with a 300 W xenon lamp through glass fibers and a UV filter (Schott UG11). The integral irradiation intensity is 0.5 mW/cm$^2$. At approximately 60 s intervals the irradiation is discontinued and the absorption spectrum is measured. The spectrum of the sample changes from yellow (optical density 1 at 300 nm, 0.4 at 400 nm and zero above 450 nm) to red, caused by a broad absorption band in the range from 400 to 550 nm (maximum optical density 0.65 at 480 nm). The time constant of the conversion is 250 s. For the reverse reaction, the UV filter is replaced by a yellow cut-on filter (Schott GG 475 with transmission above ca. 450 nm). The integral irradiation intensity in the range from 450 to 550 nm is 3 mW/cm$^2$. The irradiation causes the long-wave absorption band to disappear at 400 to 550 nm to a maximum optical density of 0.1. The time constant of the reverse reaction is 200 s. In further irradiation cycles the critical values of the optical density remain constant (at 480 nm: ca. 0.1/0.65).

EXAMPLE C4

Dot marking of a polystyrene film

The film of Example C3 is placed between 2 quartz glass plates on an xy-table and irradiated with UV light (excimer laser 308 nm, ca. 0.2 J/cm$^2$ per pulse) until saturated (red coloration). A laser beam of wavelength 488 nm ((Ar$^+$-ion laser) is focused pointwise on the film via an electrooptical switch, a monomode filament and a microscopic lens. Depending on the irradiation intensity and pulse duration, the transmission of the dots written into the film at 488 nm after irradiation is 25% to 85%. The necessary irradiation intensity for a 50% change in transmission (25 to 75%) is 0.5 W/cm$^2$. During writing, the irradiated dots exhibit orange fluorescence (500–700 nm). For reading out the transmission of a dot, an energy which is substantially reduced compared with that used for writing and which virtually does not change the transmission will suffice. Renewed UV irradiation of the film (ca. 0.2 J/cm$^2$ at 308 nm) erases the dots almost completely.

EXAMPLE C5

Recording a hologram

The film of Example C3 is placed between two quartz glass plates in the plane of the film of a holographic recorder and irradiated with UV light until completely saturated (red coloration). With an expanded, waveguided beam of an argon laser (488 nm) an object is projected vertically on to the plane of the film by means of a rainbow master hologram. A portion of the expanded beam is used as reference beam (angle of incidence ca. 30°). The irradiation intensity in the plane of the film is ca. 5 W/cm$^2$, diistributed between the reference and the object beam in the ratio of 4:1. After an irradiation time of 60 s, the irradiation intensity is substantially reduced and the object beam is faded out. The hologram recorded in the film appears with good contrast in the plane of the film. The hologram is just as clearly visible when using the white light of a spot lamp instead of laser light for reading out, in which case only the short-wave (blue) rainbow colours appear. Brightness and contrast of the hologram diminish after prolonged irradiation of the film under the reference beam.

EXAMPLE C6

Holographic recording

The film of Example C3 is placed between two quartz glass plates in the film plane of a holographic recorder. Two even beams (O and R), each having an irradiation intensity of 2.5 mW/cm², are formed from an expanded, wave-guided argon laser beam (488 nm, φ ca. 0.5 cm) and brought to coincidence at an angle of 3° in the plane of the film. A bundle of UV light (0.5 mW/cm²), coincident with O and R, is directed on to the plane of the film from a 300 W xenon lamp through a UV filter (Schott UG11) and a quartz filament. Behind the plane of the film, a detector for measuring the diffraction efficiency is mounted in the direction of the first order of diffraction of R and of the second of O. The film is converted into the red form by irradiating it for 10 minutes with UV light. After activating O and R, there occurs a monotonic increase in the diffraction efficiency from 0 to ca. 0.1% (writing) over 60 s. After discontinuing O, the diffraction efficiency increases sharply to ca. 0.12% (suppression of the destructively interfering second diffraction order of O) and then increases approximately exponentially with a time constant of ca. 60 s (overwriting). Erasure is effected by renewed UV irradiation. No diminution of the diffraction efficiency can be determined after 10 cycles. Simultaneous writing and erasing (holographic short-time memory) gives a stationary diffraction efficiency of ca. 0.05%.

What is claimed is:

1. A compound of formula V

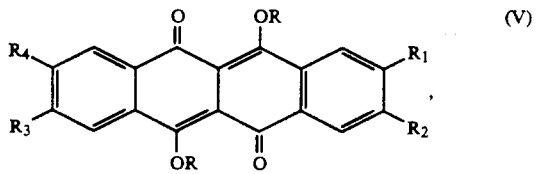

wherein

R is unsubstituted $C_6$-$C_{14}$aryl or $C_6$-$C_{14}$aryl which is substituted by $C_1$-$C_{12}$alkyl, $C_1$-$C_{12}$alkoxy, $C_1$-$C_{12}$alkylthiol, phenyl, benzyl, —CN, —CF3, halogen or —COOR$_5$; and R$_5$ is H, $C_1$-$C_{18}$alkyl, cyclohexyl, cyclopentyl, phenyl, $C_1$-$C_{12}$alkylphenyl, benzyl or $C_1$-$C_{12}$alkylbenzyl; and at least one of the substituents $R_1$ to $R_4$ is an organic thiol, sulfoxy or sulfonyl group, and the other members $R_1$ to $R_4$ are H, F, Cl or Br.

* * * * *